US009880379B2

(12) United States Patent
Saito

(10) Patent No.: US 9,880,379 B2
(45) Date of Patent: Jan. 30, 2018

(54) ENDOSCOPE LASER LIGHT FILTER ASSEMBLY

(71) Applicant: Boston Scientific Scimed, Inc., Maple Grove, MN (US)

(72) Inventor: Nathan Saito, San Jose, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 205 days.

(21) Appl. No.: 14/875,962

(22) Filed: Oct. 6, 2015

(65) Prior Publication Data

US 2016/0097925 A1    Apr. 7, 2016

Related U.S. Application Data

(60) Provisional application No. 62/060,735, filed on Oct. 7, 2014.

(51) Int. Cl.
| | |
|---|---|
| *G02B 5/20* | (2006.01) |
| *G02B 23/24* | (2006.01) |
| *G02B 7/00* | (2006.01) |
| *A61B 1/00* | (2006.01) |

(52) U.S. Cl.
CPC ...... *G02B 23/2453* (2013.01); *A61B 1/00186* (2013.01); *G02B 7/006* (2013.01)

(58) Field of Classification Search
CPC .. G02B 23/2453; G02B 7/006; A61B 1/00186
See application file for complete search history.

(56) References Cited

U.S. PATENT DOCUMENTS

| 4,863,304 A | 9/1989 | Bauer et al. |
| 2013/0301148 A1 | 11/2013 | Breidenthal et al. |

FOREIGN PATENT DOCUMENTS

| DE | 79 18 414 U1 | 10/1979 | |
| DE | 7918414 | * 10/1979 | ............... A61B 1/04 |
| DE | 87 11 421 U1 | 10/1987 | |

OTHER PUBLICATIONS

International Search Report and Written Opinion for PCT/US2015/054192, dated Jan. 4, 2016 (9 pages).

\* cited by examiner

*Primary Examiner* — Joseph P Martinez
(74) *Attorney, Agent, or Firm* — Bookoff McAndrews, PLLC

(57) ABSTRACT

An endoscope laser light filter assembly includes a filter support having opposing first and second sides, one or more circumferential flanges, and a laser light filter. The one or more circumferential flanges are positioned on the first side of the filter support and are displaced from the filter support along a central axis. The laser light filter is supported on the second side of the filter support.

18 Claims, 3 Drawing Sheets

ENDOSCOPE LASER LIGHT FILTER ASSEMBLY

CROSS-REFERENCE TO RELATED APPLICATION

The present application is based on and claims the benefit of U.S. provisional patent application Ser. No. 62/060,735, filed Oct. 7, 2014, the content of which is hereby incorporated by reference in its entirety.

FIELD OF THE INVENTION

The invention generally relates to endoscopes and, more specifically, to a laser light filter assembly for use with an endoscope to improve imaging during laser operations.

BACKGROUND

An endoscope is a medical device having a distal end that may be inserted into an internal body cavity to examine the body cavity. Conventional endoscopes include a camera that can be used to visualize the location at the distal end of the endoscope. A physician may use images produced by the camera to navigate the distal end to the desired treatment site and visualize the treatment site.

Conventional endoscopes also include one or more channels through which instruments may be inserted to perform a medical operation at the treatment site. One such instrument is a laser probe that can be used to perform a laser operation by discharging laser energy from a distal end at the treatment site. The laser operation may be used to, for example, ablate, cauterize, vaporize, coagulate, and cut tissue at the treatment site.

The camera of the endoscope is often used to visualize the laser operation being performed at the treatment site within the body cavity. In order to improve a clinician's ability to view the treatment site, camera filters designed to improve the visibility of the laser light, are typically used in combination with the camera of the endoscope.

SUMMARY

Embodiments of the invention are generally directed to a laser light filter assembly for use with an endoscope to filter light transmitted through the endoscope before imaging, and an imaging assembly that includes the laser light filter assembly and is configured for attachment to a proximal end of an imaging channel of an endoscope. One embodiment of the endoscope laser light filter assembly includes a filter support having opposing first and second sides, one or more circumferential flanges, and a laser light filter. The one or more circumferential flanges are positioned on the first side of the filter support and are displaced from the filter support along a central axis. The laser light filter is supported on the second side of the filter support.

One embodiment of the imaging assembly includes a filter assembly and an attachment member. The filter assembly includes a filter support having opposing first and second sides, one or more circumferential flanges, and a laser light filter. The one or more circumferential flanges are positioned on the first side of the filter support and are displaced from the filter support along a central axis. The laser light filter is supported on the second side of the filter support. The attachment member is configured to pinch the one or more circumferential flanges against the proximal end of the imaging channel to secure the filter assembly to the proximal end of the imaging channel.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The claimed subject matter is not limited to implementations that solve any or all disadvantages noted in the Background.

DETAILED DESCRIPTION OF ILLUSTRATIVE EMBODIMENTS

Figure 1:
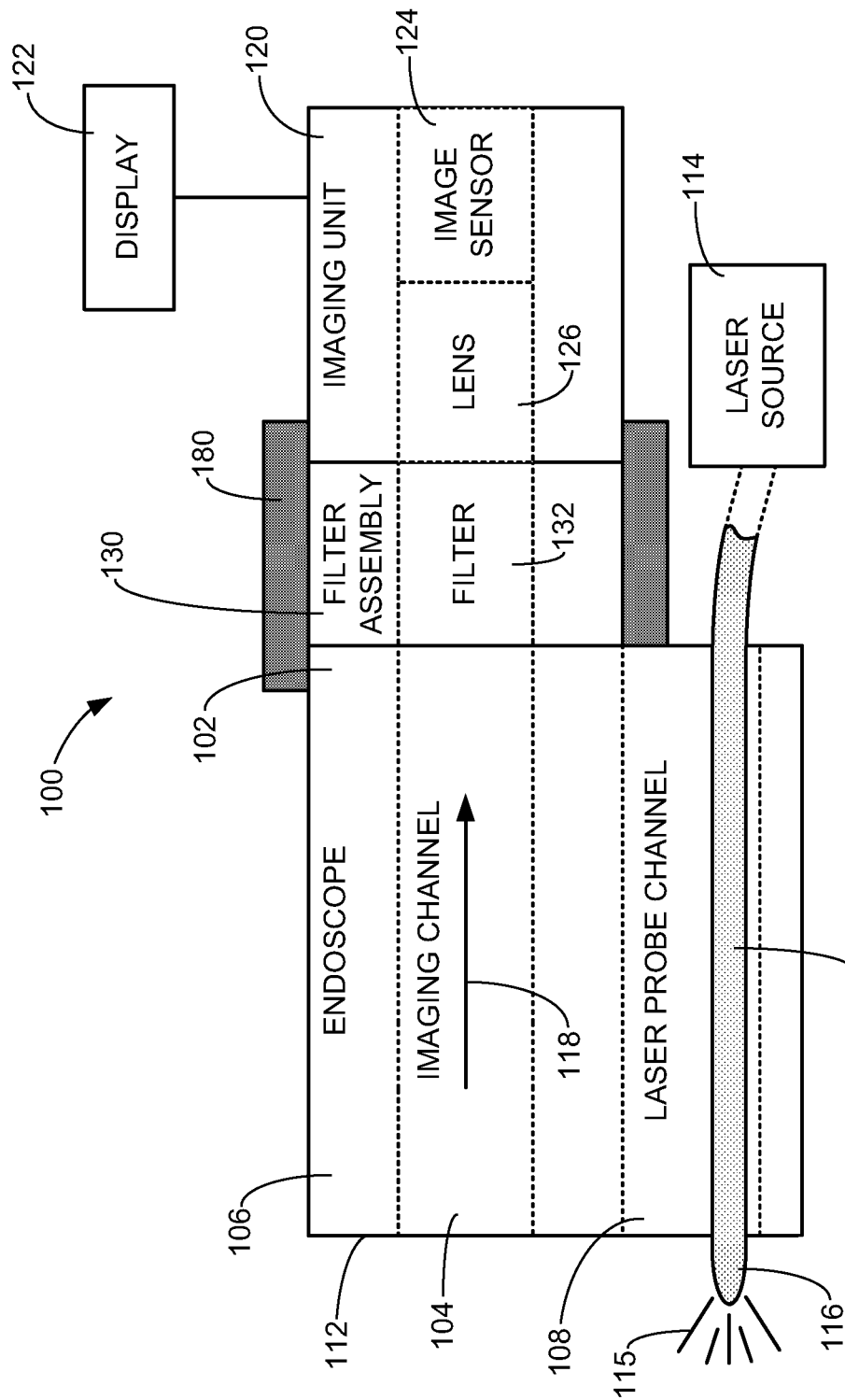
FIG. 1 is a simplified block diagram of an imaging assembly attached to an endoscope, in accordance with embodiments of the invention.

Embodiments of the invention are described more fully hereinafter with reference to the accompanying drawings. Elements that are identified using the same or similar reference characters refer to the same or similar elements. The various embodiments of the invention may, however, be embodied in many different forms and should not be construed as limited to the embodiments set forth herein. Rather, these embodiments are provided so that this disclosure will be thorough and complete, and will fully convey the scope of the invention to those skilled in the art.

Specific details are given in the following description to provide a thorough understanding of the embodiments. However, it is understood by those of ordinary skill in the art that the embodiments may be practiced without these specific details. For example, circuits, systems, networks, processes, frames, supports, connectors, motors, processors, and other components may not be shown, or shown in block diagram form in order to not obscure the embodiments in unnecessary detail.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It will be understood that when an element is referred to as being "connected" or "coupled" to another element, it can be directly connected or coupled to the other element or intervening elements may be present. In contrast, if an element is referred to as being "directly connected" or "directly coupled" to another element, there are no intervening elements present.

It will be understood that, although the terms first, second, etc. may be used herein to describe various elements, these elements should not be limited by these terms. These terms are only used to distinguish one element from another. Thus, a first element could be termed a second element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Embodiments of the invention are generally directed to a laser light filter assembly for use with an endoscope to filter light transmitted through the endoscope before imaging, and an imaging assembly that includes the laser light filter assembly and is configured for attachment to a proximal end of an imaging channel of an endoscope. In some embodiments, the filter assembly is configured for use with endoscopes during the performance of a laser operation using a laser probe that is inserted through a channel of the endoscope. In some embodiments, the laser light filter assembly includes a laser light filter that is configured to block wavelengths of the laser energy to facilitate better imaging of the laser operation through the imaging channel of the endoscope.

FIG. 1 is a simplified block diagram of an imaging assembly 100 attached to a proximal end 102 of an imaging channel 104 of an endoscope 106, in accordance with embodiments of the invention. In some embodiments, the endoscope 106 includes a laser probe channel 108, through which a laser probe 110 may be directed to a distal end 112 of the endo scope 106 to perform a laser operation at a desired treatment site of a patient. In some embodiments, the laser probe 110 is coupled to a laser source 114 that is configured to generate laser energy 115 and transmit the laser energy 115 through the probe 110, using conventional techniques. The laser energy 115 is discharged to the treatment site through a distal end 116 of the laser probe 110 to perform a laser operation at the treatment site. Exemplary laser operations include vaporization, cutting, ablation, coagulation, or other laser operations.

In some embodiments, the laser source 114 is configured to generate conventional laser energies, which are suitable for performing one or more laser operations. In some embodiments, the laser source 114 is configured to generate laser energies 115 having different wavelengths depending on the type of laser operation that is to be performed. In some embodiments, the laser source 114 comprises a laser resonator or other suitable laser generator that is configured to produce laser energy 115 having a fundamental wavelength of approximately 532 nm (nanometers), which is useful in vaporizing, ablating, and cutting operations. In some embodiments, laser energy 115 has a fundamental wavelength of 1,064 nm, which is not strongly absorbed in most tissue and penetrates deeply into the tissue, making it effective in coagulation operations.

In some embodiments, the laser source 114 comprises a yttrium-aluminum-garnet crystal rod with neodymium atoms dispersed in the YAG rod form a Nd:YAG laser element or gain medium. Other conventional laser elements may also be used to produce the desired laser energy 115.

The imaging channel 104 of the endoscope 106 facilitates imaging the treatment site at the distal end 112, including laser treatments at the treatment site that are performed using the laser probe 110, for example. In some embodiments, the imaging channel 104 is a telescopic device. In general, light 118 is transmitted through the imaging channel 104 to the proximal end 102 of the endoscope. The imaging assembly 100 is configured to support an imaging unit 120 at the proximal end 102 of the imaging channel 104 to allow the imaging unit 120 to process the light 118 and produce images of the treatment occurring at the distal end 112. In some embodiments, the imaging unit 120 produces the images on a display 122 in accordance with conventional techniques.

In some embodiments, the imaging unit 120 includes an image sensor 124 and a lens 126 that is configured to focus the light 118 on the image sensor 124. The image sensor 124 may be a conventional image sensor, such as a charge-coupled device (CCD), or other suitable image sensor. The output signal from the image sensor 124 may be processed by the imaging unit 120 or an external processor to facilitate display of the images of the treatment site at the distal end 112 of the endoscope 106 on the display 122.

During the laser operation at the distal end 112 of the endoscope 106, a portion of the laser energy 115 will be transmitted through the imaging channel 104 as the light 118, which can adversely affect the ability of the sensor 124 to produce suitable images of the treatment site and the laser operation. In some embodiments, the imaging unit 120 includes a laser light filter assembly 130 having a laser light filter 132 that is configured to block or attenuate wavelengths of the light 118 that could have an adverse effect on the images produced by the image sensor 124, before the light 118 reaches the image sensor 124. This results in improved imaging of the treatment site by the image sensor 124.

In some embodiments, the laser light filter 132 is configured to block or attenuate wavelengths corresponding to that of the laser energy 115, while allowing other wavelengths of the light 118 to pass to the image sensor 124. In some embodiments, the laser light filter 132 is configured to block wavelengths of 532 nanometers (nm), 1064 nm, or other wavelengths of the laser energy 115 produced by the laser source 114. In some embodiments, the laser light filter 132 also blocks wavelengths of electromagnetic energy that are outside the wavelength range of the laser energy 115 generated by the laser source 114.

In some embodiments, the laser light filter 132 is a conventional filter configured to block desired wavelengths of the light 118 transmitted through the imaging channel 104. Thus, the laser light filter 132 may be a glass filter or other conventional filter.

Figure 2:
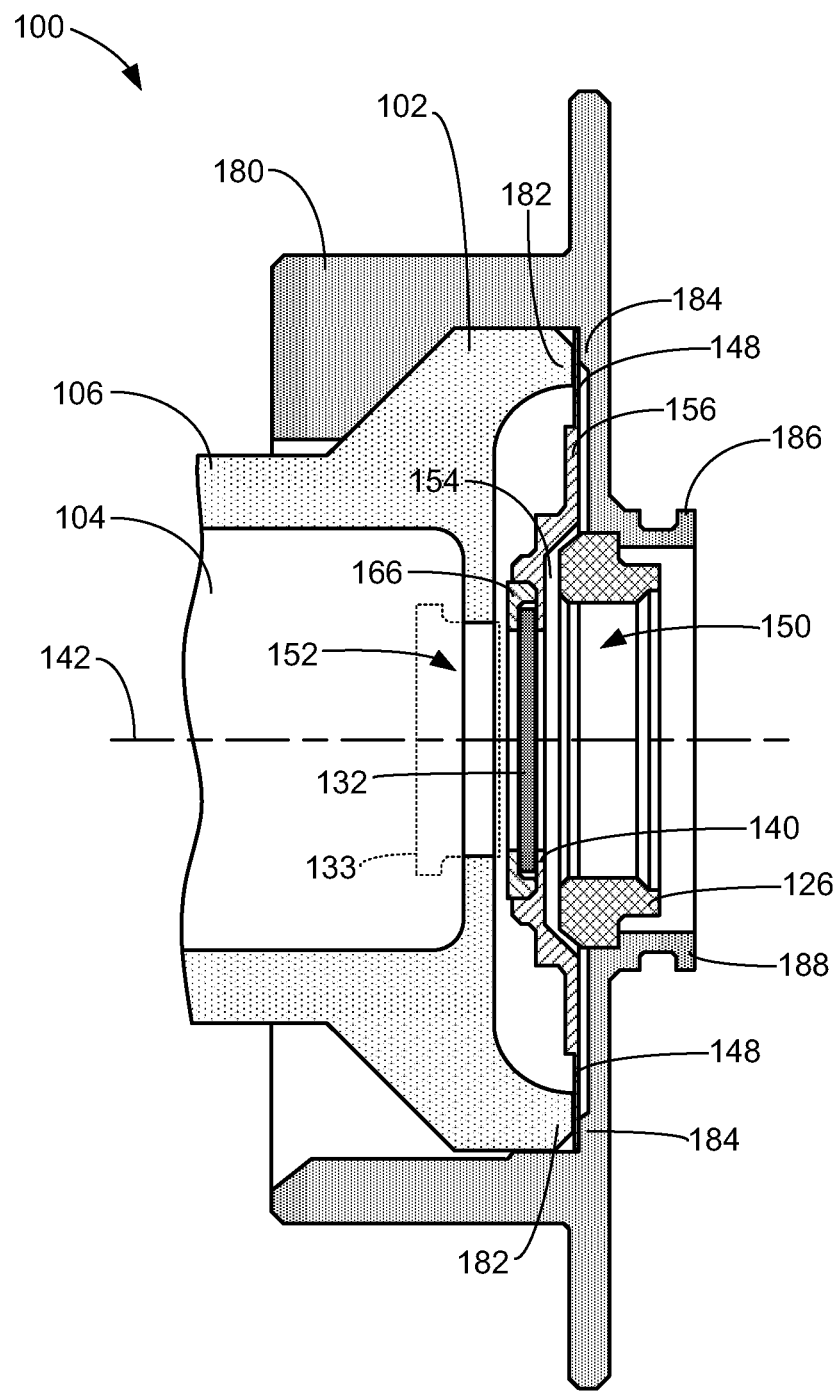
FIG. 2 is a simplified side cross-sectional view of an imaging assembly attached to a distal end of an imaging channel of an endoscope, in accordance with embodiments of the invention.
Figure 3:
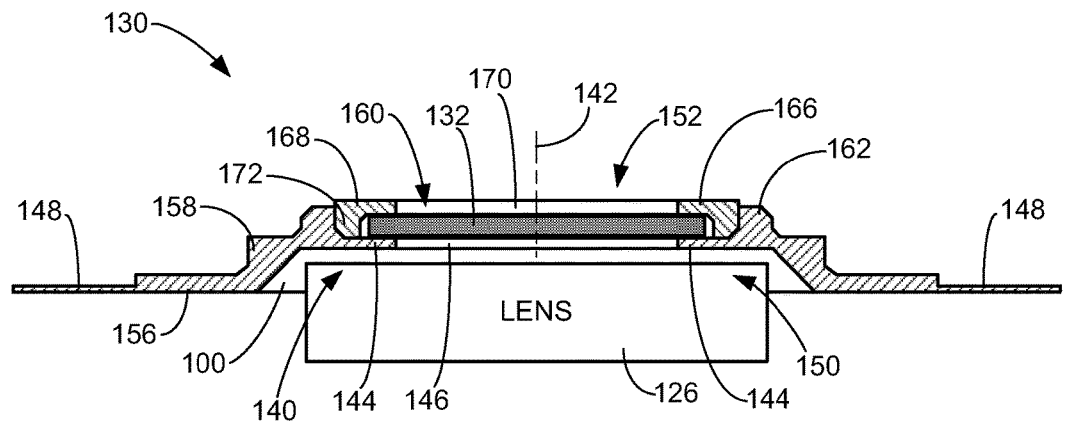
FIG. 3 is a side cross-sectional view of an endoscope laser light filter assembly, in accordance with embodiments of the invention.
Figure 4:
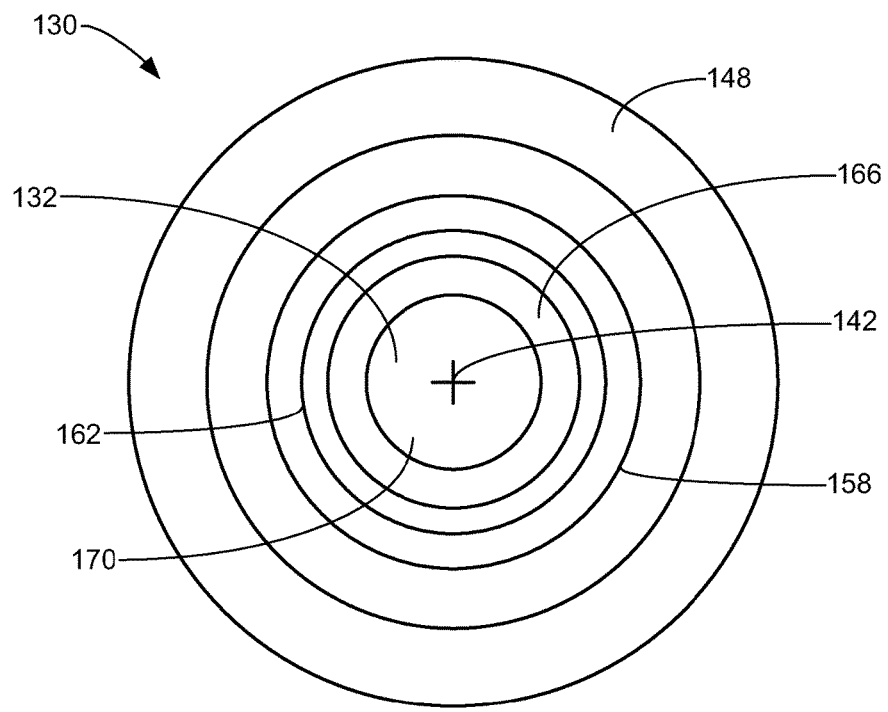
FIG. 4 is a simplified top view of the endoscope laser light filter assembly of FIG. 3.

Embodiments of the imaging assembly 100 and the laser light filter assembly 130 will be described below in greater detail with reference to FIGS. 2-4. FIG. 2 is a simplified side cross-sectional view of an imaging assembly 100 attached to the proximal end 102 of the imaging channel 104 of the endoscope 106, in accordance with embodiments of the invention. FIG. 3 is a side cross-sectional view of a laser light filter assembly 130 in accordance with embodiments of the invention. FIG. 4 is a top-view of the laser light filter assembly 130 of FIG. 3.

The endoscope laser light filter assembly 130 is generally configured to support the laser light filter 132 for mounting to the proximal end 102 of the imaging channel 104, which may include a lens 133 as indicated in phantom lines in FIG. 2. This allows the filter 132 to filter the light 118 before it reaches the imaging unit 120.

In some embodiments, the filter assembly 130 includes a filter support 140 that is configured to support the filter 132 relative to a central axis 142, as shown in FIG. 3. In some embodiments, the filter support 140 comprises one or more flanges 144 that support the filter 132 in a plane that is substantially perpendicular to the central axis 142, and an aperture 146. In some embodiments, the one or more flanges 144 comprise an annular flange or equivalent structure. In some embodiments, the annular flange 144 is concentric to the central axis 142, as shown in FIGS. 3 and 4. Other configurations for the one or more flanges 144 may also be used.

In some embodiments, the filter assembly 130 includes one or more circumferential flanges 148 located on a side 150 of the filter support 140 that is opposite the side 152 of the filter support 140, on which the filter 132 is supported. The one or more flanges 148 extend in a radial direction relative to the central axis 142 and are oriented substantially perpendicular to the central axis 142, as shown in FIG. 3. In some embodiments, the one or more flanges 148 comprise an annular flange or equivalent structure. In some embodiments, the annular circumferential flange 148 is substantially concentric to the central axis 142, as shown in FIG. 3. Other configurations for the one or more flanges 148 may also be used.

In some embodiments, the one or more flanges 148 are displaced from the filter support 140 along the central axis 142, as shown in FIG. 3. In some embodiments, the flange 148 is displaced from the filter support 140 along the central axis 142 a distance of 1-5 millimeters (mm), such as 1 mm, 2 mm, 3 mm, 4 mm, or 5 mm, for example.

In some embodiments, the filter assembly 130 includes a lens recess 154 located on the side 150 of the filter support 140. In some embodiments, the lens recess 154 accommodates the lens 126 of the imaging unit 120, as shown in FIG. 2 and indicated schematically in FIG. 3. In some embodiments, the lens recess 154 provides an opening on the side 150 of the filter support 140 having a diameter extending in a plane that is perpendicular to the central axis 142 that is larger than the diameter of the aperture 146. In some embodiments, the one or more flanges 148 extend radially from the lens recess 154 relative to the central axis 142.

In some embodiments, the filter assembly 130 comprises a base member 156 that includes the filter support 140 and the one or more flanges 148, as shown in FIG. 3. In some embodiments, the lens recess 154 is defined by at least one lens recess side wall 158 of the base member 156, which extends from the circumferential flange 148 along the central axis 142 to the filter support 140. In some embodiments, the at least one recessed side wall 158 is an annular side wall that creates a conical or cylindrical lens recess 154, as shown in FIGS. 3 and 4.

In some embodiments, laser light filter 132 is supported on the side 152 of the filter support 140 within a filter recess 160. In some embodiments, the filter recess 160 is defined by at least one filter recess side wall 162 that extends from the filter support 140 along the central axis 142. In some embodiments, the at least one filter recess side wall 162 is a portion of the base member 156, as shown in FIG. 3. In some embodiments, the at least one filter recess side wall 162 comprises an annular side wall, as best shown in FIG. 4.

In some embodiments, the filter assembly 130 includes a cover member 166 that is attached to the base member 156 on the side 152 of the filter support 140, as shown in FIG. 3. In some embodiments, the cover member 166 operates to secure the laser light filter 132 within the filter recess 160.

In some embodiments, the cover member 166 sandwiches the filter 132 against the filter support 140. In some embodiments, the cover member 166 includes one or more flanges 168 that pinch a peripheral portion of the filter 132 against the filter support 140. In some embodiments, the one or more flanges 168 include an annular flange, as shown in FIG. 3, or other suitable structure. In some embodiments, the annular flange 168 is substantially concentric with the central axis 142.

In some embodiments, the cover member 166 includes an aperture 170. In some embodiments, the aperture 170 is concentric with the central axis 142.

In some embodiments, a portion 172 of the cover member 166 extends into the filter recess 160, as shown in FIG. 3. Alternatively, the portion 172 could be configured to extend around the perimeter of the one or more filter recess side walls 162. In some embodiments, the portion 172 forms an interference fit with the one or more side walls 162 of the base member 156 to secure the cover member 166 to the base member 156. Alternatively the cover member 166 may be secured to the base member 156 using an adhesive, a weld, or other suitable fastening technique.

In some embodiments, the base member 156 and the cover member 166 are formed from the same or different materials. In some embodiments, the base member and the cover member comprise aluminum.

The imaging assembly 100 generally comprises the endoscope laser light filter assembly 130 formed in accordance with one or more embodiments described herein, and an attachment member 180 that is configured to secure the filter assembly 130 to the endoscope 106, such as to the proximal end 102 of the imaging channel 104, as shown in FIG. 2. In some embodiments, the one or more flanges 148 are pinched between the flange 182 of the imaging channel 104 and at least one portion 184 of the attachment member 180, as shown in FIG. 2. In some embodiments, the attachment member 180 secures the filter assembly 130 to the proximal end 102 of the endoscope imaging channel 104 such that the central axis 142 of the filter assembly 130 is substantially concentric to the imaging channel 104, as shown in FIG. 2.

In some embodiments, the attachment member 180 is in the form of an attachment ring, which receives the proximal end 102 of the imaging channel 104 and pinches the one or more circumferential flanges 148 against at least one flange 182 of the imaging channel 104, or a portion of the endoscope 106, in response to rotation of the attachment ring 180 about the central axis 142. Other types of attachment members 180 may also be used.

In some embodiments, the endoscope 106 only contacts the laser light filter assembly 130 at the one or more circumferential flanges 148, as shown in FIG. 2. In some embodiments, this contact is only by the at least one flange 182. In some embodiments, the attachment member 180 only contacts the laser light filter assembly 130 at the one or more circumferential flanges 148, as shown in FIG. 2. In some embodiments, this contact is only by the at least one portion 184.

In some embodiments, the attachment member 180 provides support for the lens 126 of the imaging unit 120, as shown in FIG. 2. In some embodiments, the attachment member 180 supports the lens 126, such that the lens 126 protrudes into the lens recess 154, as shown in FIGS. 2 and 3. Thus, a portion of the lens 126 extends along the central axis 142 into the recess 154 through a plane extending perpendicularly to the central axis 142 and through the one or more flanges 148, as shown in FIGS. 2 and 3.

In some embodiments, the attachment mechanism 180 includes a connector 186 at a proximal end 188 that is configured for connecting the image sensor 124 or a camera containing the image sensor 124. In some embodiments, the connector 186 supports the image sensor in alignment with the central axis 142.

In some embodiments, the aperture 170, the laser filter 132, the aperture 146, the circumferential flange 148, the filter support 140, the filter recess 160, the lens recess 154, the imaging channel 104, and/or the lens 126 are substantially concentric to the central axis 142 when the attachment member 180 is secured to the proximal end 102 of the endoscope imaging channel 104, as shown in FIG. 2. In some embodiments, the central axis 142 extends through the aperture 170, the laser filter 132, the filter recess 160, the lens recess 154, and the lens 126. As a result, in some embodiments, the filter assembly 130 is supported such that the light 118 transmitted through the imaging channel 104 travels along the central axis 142 from the side 152 of the filter support 140 through the filter 132, past the filter support 140, and through the lens 126.

The passage of the light 118 through the laser filter 132 of the assembly 130 blocks or attenuates some of the wavelengths of the light 118, such as those corresponding to the laser energy 115 (FIG. 1), before the sensor 124 is exposed to the light 118. This at least reduces the magnitude of wavelengths of the light 118 that could adversely affect the images formed using the output from the image sensor 124. As a result, the image sensor 142 is capable of generating higher quality images during laser operations than would be possible without the laser filter assembly 130 and the laser light filter 132.

The foregoing examples have focused on embodiments of a laser light filter assembly 130 for use with an endoscope 106 to filter light 118 transmitted through an imaging channel 104 of an endoscope to improve imaging of a treatment site during a laser or other operation using an image sensor 124. Other embodiments have focused on an imaging assembly 100 that supports the laser light filter assembly 130 at a proximal end 102 of an imaging channel 104 of an endoscope. In some embodiments, the filter assembly 130 is configured for use during the performance of a laser operation using a laser probe 110 that is inserted through a channel 108 of the endoscope 106. In some embodiments, the laser light filter assembly 130 includes a laser light filter 132 that is configured to block wavelengths of the laser energy 115 discharged from the laser probe 110 to facilitate better imaging of the laser operation through the imaging channel 104 of the endoscope 106 by the image sensor 124.

Although embodiments of the present invention has been described with reference to preferred embodiments, workers skilled in the art will recognize that changes may be made in form and detail without departing from the spirit and scope of the invention.

What is claimed is:

1. An endoscope laser light filter assembly comprising:
    a filter support having opposing first and second sides;
    one or more circumferential flanges on the first side of the filter support and displaced from the filter support along a central axis; and
    a laser light filter supported on the second side of the filter support,
    wherein the laser light filter is configured to block or attenuate laser light having at least one wavelength selected from the group consisting of 532 nm or 1064 nm.

2. The filter assembly according to claim 1, wherein the filter assembly comprises:
    a base member comprising the filter support, the one or more circumferential flanges, and a lens recess extending from the first side of the filter support along the central axis to the one or more circumferential flanges; and
    a cover member attached to the base member on the second side of the filter support, wherein the laser light filter is sandwiched between the base member and the cover member.

3. The filter assembly according to claim 2, wherein the central axis extends through an aperture of the cover member, an aperture of the filter support, the lens recess, and the laser light filter.

4. The filter assembly according to claim 2, wherein the one or more circumferential flanges extend in a plane that is perpendicular to the central axis.

5. The filter assembly according to claim 2, wherein the lens recess is defined by at least one lens recess side wall of the base member extending from the one or more circumferential flanges along the central axis to the filter support.

6. The filter assembly according to claim 5, wherein the at least one lens recess side wall comprises an annular side wall.

7. The filter assembly according to claim 2, wherein the laser light filter is supported on the filter support within a filter recess defined by at least one filter recess side wall of the base member extending from the filter support along the central axis.

8. The filter assembly according to claim 7, wherein the at least one filter recess side wall comprises an annular side wall.

9. The filter assembly according to claim 7, wherein at least a portion of the cover member extends into the filter recess.

10. An imaging assembly configured for attachment to a proximal end of an imaging channel of an endoscope, the imaging assembly comprising:
    a filter assembly comprising:
        a filter support having opposing first and second sides;
        one or more circumferential flanges on the first side of the filter support and displaced from the filter support along a central axis; and
        a laser light filter supported on the second side of the filter support; and
    an attachment member configured to pinch the one or more circumferential flanges against the proximal end of the imaging channel to secure the filter assembly to the proximal end of the imaging channel,
    wherein the filter assembly includes a lens recess extending from the first side of the filter support along the central axis to the one or more circumferential flanges; and
    wherein the endoscope imaging assembly includes an imaging unit comprising a lens, which protrudes along the central axis into the lens recess.

11. The imaging assembly according to claim 10, wherein the imaging unit comprises an imaging sensor adjacent the lens.

12. The imaging assembly according to claim 10, wherein the one or more circumferential flanges extend in a plane that is perpendicular to the central axis.

13. The imaging assembly according to claim 10, wherein the laser light filter is configured to block or attenuate laser light having at least one wavelength selected from the group consisting of 532 nm or 1064 nm.

14. The imaging assembly according to claim 10, wherein the filter assembly comprises:
   a base member comprising the filter support, the one or more circumferential flanges, and the lens recess; and
   a cover member attached to the base member on the second side of the filter support, wherein the laser light filter is sandwiched between the base member and the cover member.

15. The imaging assembly according to claim 14, wherein the central axis extends through an aperture of the cover member, an aperture of the filter support, the lens recess, and the laser light filter.

16. The imaging assembly according to claim 14, wherein the lens recess is defined by at least one lens recess side wall of the base member extending from the one or more circumferential flanges along the central axis to the filter support.

17. The imaging assembly according to claim 14, wherein the laser light filter is supported on the filter support within a filter recess defined by at least one filter recess side wall of the base member extending from the filter support along the central axis.

18. The imaging assembly according to claim 17, wherein at least a portion of the cover member extends into the filter recess.

* * * * *